United States Patent [19]

Chen et al.

[11] Patent Number: 5,208,352

[45] Date of Patent: May 4, 1993

[54] PROCESS FOR PREPARING THE R- AND S-ISOMERS OF 2-HYDROXY-METHYL-2-OCTADECYLOX- YMETHYL-TETRAHYDROFURAN AND THEIR USE IN PREPARING STEREOISOMERS OF PHARMACOLOGICALLY ACTIVE COMPOUNDS

[75] Inventors: Chung-Pin Chen; Prasad K. Kapa, both of Parsippany; William J. Houlihan, Mountain Lakes, all of N.J.

[73] Assignee: Sandoz Ltd., Basle, Switzerland

[21] Appl. No.: 862,137

[22] Filed: Apr. 2, 1992

[51] Int. Cl.$^5$ .................. C07D 307/06; C07D 303/14; C07D 303/18; C07D 301/12
[52] U.S. Cl. .................... 549/502; 549/529; 549/554
[58] Field of Search ........................ 549/502

[56] References Cited

U.S. PATENT DOCUMENTS 4,673,672  6/1987  Houlihan et al. ................ 514/95

FOREIGN PATENT DOCUMENTS 462935  12/1991  European Pat. Off. .

OTHER PUBLICATIONS

*Tetrahedron Letters,* No. 31, pp. 2741–2744 (1978).
*Chemistry Letters,* pp. 1717–1720 (1988).
*Tetrahedron Letters,* vol. 31, No. 4, pp. 445–448 (1990).
*Tetrahedron:Asymmetry,* vol. 1, No. 7, pp. 421–424 (1990).

*Primary Examiner*—Joseph E. Evans
*Attorney, Agent, or Firm*—Robert S. Honor; Melvyn M. Kassenoff; Joseph J. Borovian

[57] ABSTRACT

An improved process for preparing the R- and S-isomers of 2-hydroxymethyl-2-octadecyloxymethyl-tetrahydrofuran, a critical step of which involves the preparation of the R- and S-isomers of 2-[3-(1-methoxy-1-methylethoxy)]propyl-oxiranemethanol employing metal-catalyzed Sharpless epoxidation. In addition, the invention relates to the use of the R- and S-isomers of 2-hydroxymethyl-2-octadecyloxymethyl-tetrahydrofuran in preparing stereoisomers of pharmacologically active compounds, and to the R- and S-isomers of 2-[3-(1-methoxy-1-methylethoxy)]-propyl-oxiranemethanol as novel compounds.

30 Claims, No Drawings

PROCESS FOR PREPARING THE R- AND S-ISOMERS OF 2-HYDROXY-METHYL-2-OCTADECYLOXYMETHYL-TETRAHYDROFURAN AND THEIR USE IN PREPARING STEREOISOMERS OF PHARMACOLOGICALLY ACTIVE COMPOUNDS

The present invention relates to a process for preparing the R- and S-isomers of 2-hydroxymethyl-2-octadecyloxymethyl-tetrahydrofuran, a critical step of which involves the preparation of the R- and S-isomers of 2-[3-(1-methoxy-1-methylethoxy)]propyl-oxiranemethanol employing metal-catalyzed Sharpless epoxidation. In addition, the present invention relates to the use of the R- and S-isomers of 2-hydroxymethyl-2-octadecyloxymethyl-tetrahydrofuran in preparing stereoisomers of pharmacologically active compounds, and to the R- and S-isomers of 2-[3-(1-methoxy-1-methylethoxy)]propyl-oxiranemethanol as novel compounds.

As is well known, many pharmacologically active compounds occur as a racemic mixture. Moreover, despite the fact that the desired pharmacological activity usually resides in one enantiomer, mixtures of enantiomers are employed because the prohibitive cost of separation exceeds the potential advantage of a possible increase in activity. However, it is quite apparent that many pharmacologists are becoming increasingly aware of other implications in the administration of racemic mixtures wherein one of the enantiomers has to be regarded as an impurity which may not only be devoid of the desired therapeutic effect but, more importantly, may contribute unwanted physiological effects including toxicity.

Numerous research endeavors have been directed to processes for producing specific stereoisomers of pharmacologically active compounds, and such processes are well documented in the patent and non-patent literature. Prominent among these are processes involving Sharpless epoxidation and the use of enzymes to induce stereospecific transformations. For example, in Tetrahedron Letters, No. 31, pgs. 2741–2744 (1978), there is described the preparation of certain tetrahydrofurans exhibiting high stereospecificity employing the Sharpless procedure, which tetrahydrofurans are valuable intermediates in the synthesis of polyether antibiotics such as lasalocids and monensins. In Chemistry Letters, pgs. 1717–1720 (1988), there is described the synthesis of certain optically active cis-2,5-disubstituted tetrahydrofuran derivatives by the enzyme-catalyzed asymmetric hydrolysis of the meso-diesters derived from cis-2,5-bis(hydroxymethyl)tetrahydrofuran. Similarly, in Tetrahedron Letters, Vol. 31, No. 4, pgs. 445–448 (1990), there is described the synthesis of certain optically active monobutyric esters by the enzymatic hydrolysis of the mesodibutyrates of bis(hydroxymethyl)-tetrahydrofurans. In addition, in Tetrahedron:Asymmetry, Vol. 1, No. 7, pgs. 421–424 (1990), there is described the synthesis of the R-isomers of two well-known hypoglycemic agents, viz., etomoxir and palmoxirate, employing the enzyme-catalyzed enantiotopic differentiation of certain prochiral 2-substituted glycerols. Moreover, European Patent application 462,935 discloses a process for preparing the (R) stereoisomer of 2,2-bis(hydroxymethyl)-tetrahydrofuran, monobutyrate comprising subjecting the dibutyric ester of 2,2-bis(hydroxymethyl)-tetrahydrofuran to enzymatic hydrolysis.

In connection with certain anti-tumor compounds disclosed in U.S. Pat. No. 4,673,672, it was desired to obtain certain optically pure intermediates, viz., the R- and S-isomers of 2-hydroxymethyl-2-octadecyloxymethyl-tetrahydrofuran. Although European Patent application 462,935 describes a suitable process for preparing said isomers, there was a need to develop a more practical process. To this end, the instant invention represents a more efficient and economic process for preparing said isomers in good yields and high optical purity, which isomers are valuable intermediates in the preparation of specific stereoisomers of pharmacologically active compounds.

In accordance with the process of the instant invention, the R-isomer of 2-hydroxymethyl-2-octadecyloxymethyl-tetrahydrofuran is prepared by a six-step process as depicted below:

STEP 1

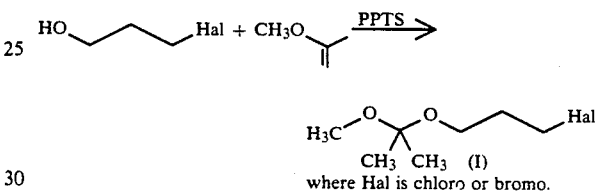

where Hal is chloro or bromo.

STEP 2

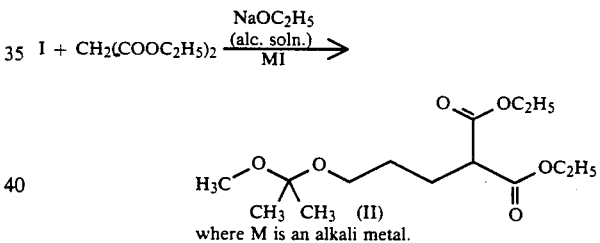

where M is an alkali metal.

STEP 3

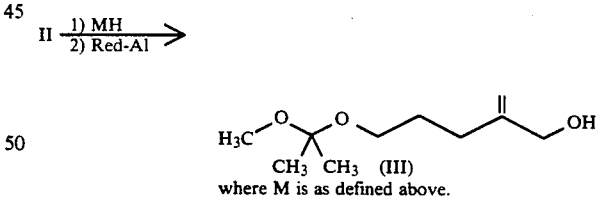

where M is as defined above.

STEP 4

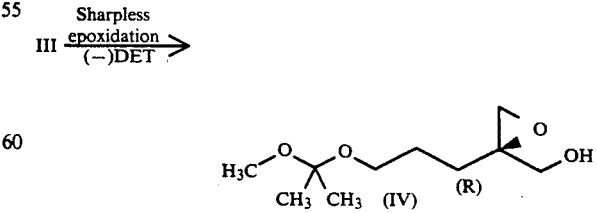

STEP 5

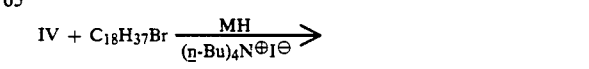

-continued

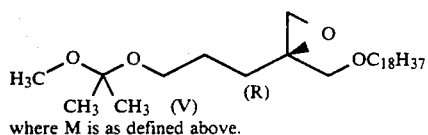
where M is as defined above.

STEP 6

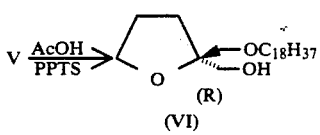

With respect to the individual steps, Step 1 concerns the reaction of either 3-chloro or 3-bromopropanol (sodium bicarbonate treated) with 2-methoxypropene in the presence of the pyridinium salt of p-toluenesulfonic acid (PPTS) to yield a compound of formula I, i.e., either 1-chloro- or 1-bromo-3-(1-methoxy-1-methylethoxy)-propane. The reaction is conducted at a temperature of between −30° and 30° C. for a period of between 1 and 4 hours.

Step 2 involves the alkylation alcoholic solution of sodium ethoxide) of diethylmalonate with a compound prepared in Step 1, i.e., a compound of formula I, in the presence of an alkali metal iodide, preferably sodium iodide, to yield the substituted malonic diester of formula II, viz., the diethyl ester of 3-(1-methoxy-1-methylethoxy)=propyl-1,3-propanedioic acid. The preparation of the diester compound of formula II is conducted at a temperature of between 60° and 100° C. for a period of between 3 and 12 hours.

Step 3 involves, in a first part, the reaction of the compound prepared in Step 2, i.e., the substituted malonic diester of formula II, with an alkali metal hydride (60% dispersion in mineral oil), preferably sodium hydride, in the presence of an inert organic solvent, e.g., an aromatic hydrocarbon such as toluene, at reflux temperature for a period of between 2 and 6 hours. The second part of Step 3 concerns reducing the compound prepared in the first part with Red-Al ® (sodium bis(2-methoxyethoxy)aluminum hydride) in the presence of an aromatic hydrocarbon such as toluene to yield the allylic alcohol of formula III, viz., 5-(1-methoxy-1-methylethoxy)-2-methylene-1-pentanol. This reaction is conducted at a temperature of between 70° and 100° C. for a period of between 1 and 3 hours.

Step 4 involves subjecting the compound prepared in the second part of Step 3, i.e., the allylic alcohol of formula III, to metal-catalyzed asymmetric Sharpless epoxidation employing a system consisting of titanium tetraisopropoxide, (−)-diethyl tartrate (unnatural DET) and t-butylhydroperoxide to yield the epoxy alcohol of formula IV, viz., the R-isomer of 2-[3-(1-methoxy-1-methylethoxy)]propyl-oxiranemethanol. The epoxidation is carried out in the presence of a mixture of inert, organic solvents, e.g., a mixture of isooctane and an aliphatic chlorinated hydrocarbon such as methylene chloride. Alternatively, the epoxidation is carried out in methylene chloride alone. The epoxidation is carried out at a temperature of between −30° and −10° C. for a period of between 4 and 20 hours.

Step 5 concerns the alkylation of the epoxy alcohol prepared in Step 4, i.e., the compound of formula IV, with n-octadecyl bromide in the presence of an alkali metal hydride (60% dispersion in mineral oil), preferably sodium hydride, and tetrabutylammonium iodide to yield the compound of formula V, viz., the R-isomer of 2-[3-(1-methoxy-1-methylethoxy)]-propyl-2-[(octadecyloxy)methyl]-oxirane. The alkylation is conveniently carried out in the presence of an inert, organic solvent, e.g., a cyclic ether such as tetrahydrofuran, at a temperature of from 0° C. to the reflux temperature of the solvent for a period of between 5 and 16 hours.

The last step, viz., Step 6, involves the reaction of the oxirane compound prepared in Step 5, viz., the compound of formula V, with acetic acid in the presence of PPTS to yield the desired tetrahydrofuran compound of formula VI, viz., the R-isomer of 2-hydroxymethyl-2-octadecyloxymethyl-tetrahydrofuran. The reaction is conducted at a temperature of between 15° and 40° C. for a period of between 18 hours and 3 days.

The S-isomer of 2-hydroxymethyl-2-octadecyloxymethyl-tetrahydrofuran is prepared in essentially the same manner as the corresponding R-isomer, i.e., by the six-step process described above, the only difference being the use of (+)-diethyl tartrate, (natural DET) in place of (−)-diethyl tartrate in the metal-catalyzed asymmetric Sharpless epoxidation in Step 4 above to yield the corresponding S-isomer of the epoxy alcohol of formula IV, viz., the S-isomer of 2-[3-(1-methoxy-1-methylethoxy)]propyl-oxiranemethanol.

Employing the S-isomer of the epoxy alcohol of formula IV, and carrying out the alkylation reaction described above in Step 5 yields the corresponding S-isomer of formula V, viz., the S-isomer of 2-[3-(1-methoxy-1methylethoxy)]-propyl-2-[(octadecyloxy)methyl]-oxirane.

Similarly, employing the S-isomer of the oxirane compound of formula V, and carrying out the reaction described above in Step 6 yields the desired tetrahydrofuran compound, viz., the S-isomer of 2-hydroxymethyl-2-octadecyloxymethyl-tetrahydrofuran.

The 3-chloro or 3-bromopropanol and the 2-methoxypropene employed as starting materials in Step 1 and the diethylmalonate employed in Step 2 are known and commercially available.

Although the product of each reaction described above may, if desired, be purified by conventional techniques such as recrystallization (if a solid), the crude product of one reaction is often employed in the following reaction without purification.

As indicated above, the R- and S-isomers of 2-hydroxymethyl-2-octadecyloxymethyl-tetrahydrofuran are valuable intermediates in the preparation of specific stereoisomers of pharmacologically active compounds, e.g., the anti-tumor compounds disclosed in U.S. Pat. No. 4,673,672.

More particularly, and with respect to the specific compound of Example 5 of said U.S. patent for purposes of illustration, it can be seen that said compound contains an asymmetric carbon atom and, therefore, the compound depicted is a mixture of two stereoisomers, viz., the (R) and (S) isomers. By employing the compound of formula VI above, viz., the R-isomer of 2-hydroxymethyl-2-octadecyloxymethyltetrahydrofuran, the (S) stereoisomer of the compound of Example 5 may be prepared by phosphorylcholinating the compound of formula VI in a two-part reaction as depicted below:

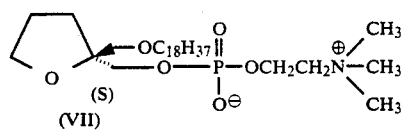

The first part involves the reaction of the compound of formula VI with phosphorus oxychloride in the presence of an amine base such as pyridine or triethylamine. The reaction is conveniently carried out in the presence of an inert, organic solvent, e.g., a halogenated hydrocarbon such as methylene chloride, at a temperature of from 0° to 40° C. for a period of between 6 and 24 hours.

The second part involves the reaction of the product produced in the first step with Choline reagent (i.e., ethanaminium,2-hydroxy-N,N,N-trimethyl-4-methylbenzenesulfonate) in the presence of an amine base such as pyridine or triethylamine and a catalytic amount of 4-dimethylaminopyridine to yield the (S) isomer of the compound of formula VII. The reaction is conveniently carried out at a temperature of from 10° to 40° C. for a period of between 16 hours and 4 days.

Similarly, the (R) stereoisomer of the compound of Example 5 may be prepared in essentially the same manner as the (S) stereoisomer, i.e., by the two-part reaction described above, the only difference being the use of the S-isomer of the compound of formula VI in place of the R-isomer.

The corresponding R- and S-isomers of the epoxy alcohol of formula IV are novel compounds and, as such, also form a part of this invention.

The following examples are for purposes of illustration only and are not intended to limit in any way the scope of the instant invention.

EXAMPLE 1

The following describes the preparation of the R-isomer of 2-hydroxymethyl-2-octadecyloxymethyl-tetrahydrofuran.

(a) Preparation of
1-Chloro-3-(1-methoxy-1-methylethoxy)-propane.

To a 1-liter, 4-necked round-bottomed flask, equipped with a mechanical stirrer, nitrogen inlet, internal thermometer, addition funnel and cooling bath (−20° to −25° C.), is added 288.4 g (4.0 mol) of 2-methoxypropene and 0.502 g (0.0002 mol) of the pyridinium salt of p-toluene sulfonic acid. To the cooled solution is then slowly added, under a nitrogen flow over a period of 1 hour, 189.0 g (2.0 mol) of 3-chloropropanol. The reaction mixture is then stirred at −20° to −25° C. for 1 hour and then warmed to 0° C. To the reactor is then added a mixture of 25 ml of a saturated aqueous sodium bicarbonate solution and 425 ml of a saturated aqueous sodium chloride solution. The resultant mixture is then transferred to a separatory funnel and the layers are separated. The organic layer is then concentrated in vacuo at 40° C. and the resultant clear light oil is dried at room temperature under high vacuum for 3 hours to yield the desired compound (97.4% yield; and 98.06% purity).

(b) Preparation of the Diethyl Ester of
3-(1-Methoxy-1-methylethoxy)propyl-1,3-propanedioic Acid To a 5-liter, 4-necked round-bottomed flask, equipped with a mechanical stirrer, nitrogen inlet, internal thermometer, addition funnel, heating mantle and condenser, is added 711 g (2.19 mol) of sodium ethoxide (21% in ethyl alcohol). After heating to a temperature between 80° and 82° C., 351.7 g (2.19 mol) of diethyl malonate is then added over a period of 10 minutes. The resultant mixture is then heated to 82° C. and maintained at this temperature for 1 hour. 305 g (1.79 mol) of the compound prepared in a) above is then added over a 15 minute period, after which time 41.1 g (0.274 mol) of sodium iodide is added. The reaction mixture is then heated to 82° C., maintained at this temperature for 10 hours, and then cooled to room temperature. To the reactor is then added 600 ml of water and the resultant mixture is then transferred to a separatory funnel and extracted with two 1.5 L portions of heptane. The combined organic extracts are then concentrated in vacuo at 40° C. and to the resultant light yellow oil is added 400 ml of toluene. The resultant solution is then concentrated in vacuo at 40° C. and the resultant light yellow oil is dried at room temperature under high vacuum for 16 hours to yield the desired compound (∼85% yield; and 82.63% purity).

(c) Preparation of
5-(1-Methoxy-1-methylethoxy)-2-methylene-1-pentanol

To a 12-liter, 4-necked round-bottomed flask, equipped with a mechanical stirrer, nitrogen inlet, internal thermometer, addition funnel, heating mantle and condenser, is added 138.4 g (3.46 mol) of sodium hydride (60% dispersion in mineral oil) in 1.7 L of toluene. The suspension is then heated to a temperature between 85° and 90° C. and to the heated suspension is added, over a period of 40 minutes while the temperature is maintained between 85° and 90° C., 646 g (1.79 mol) of the compound prepared in b) above. The resultant suspension is then heated to 110° C. and maintained at this temperature, with stirring, for 3 hours. The suspension is then cooled to a temperature between 85° and 90° C. and 1.038 L (3.53 mol) of a 3.4M solution of Red-Al ® in toluene is added at a rate such that the temperature is maintained between 85° and 90° C. The reaction mixture is then heated to 90° C. and maintained at this temperature for 1 hour, after which time it is cooled to a temperature between 5° and 10° C. To the cooled mixture is slowly added 1.2 L of a 1N sodium hydroxide solution at a rate such that the temperature does not exceed 30° to 35° C. The resultant mixture is then stirred at room temperature for 18 hours, after which time 1 L of heptane is added. This mixture is then stirred for 15 minutes and the layers are separated. The aqueous layer is then transferred to a separatory funnel and extracted with two 1 L portions of heptane. The combined organic layers are then washed with two 1 L portions of 1N sodium hydroxide solution and a mixture of 100 ml of a saturated aqueous sodium bicarbonate solution and 900 ml of a saturated aqueous sodium chloride solution. The resultant mixture is then transferred to a separatory funnel and the layers are separated. The organic layer is then concentrated in vacuo at 40° C. and the resultant oil is dried at room temperature under high vacuum for 3 hours to yield the desired compound (50% yield; and 82% purity).

(d) Preparation of the R-isomer of 2-[3-(1-Methoxy-1-methylethoxy)]propyl-oxiranemethanol.

To a 12-liter, 4-necked round-bottomed flask, equipped with a mechanical stirrer, internal thermometer, addition funnel and nitrogen inlet, is added 29.4 g (0.142 mol) of (−)-diethyl tartrate (unnatural DET), 30 g of powdered molecular sieves (4A) and 32.3 ml (0.106 mol) of titanium tetraisopropoxide in 1.2 L of methylene chloride at 0° C. The mixture is then stirred for 1 hour, after which time 67 gresultant solution is then stirred, cooled to −20° C. and to the cooled suspension is slowly added 130 ml (0.715 mol) of a 5.5M solution of t-butyl hydroperoxide in isooctane. The mixture is then stirred for 1 hour, after which time 67 g (0.356 mol) of the compound prepared in c) above in 100 ml of methylene chloride is added dropwise, over a period of 1 hour. The resultant suspension is then stirred for 4.5 hours at a temperature between −22° and −20° C., after which time 300 ml of a 5N sodium hydroxide solution is added, while the temperature is maintained at −20° C. The suspension is then warmed to room temperature and stirred at room temperature for 16 hours. 50 g of Celite is then added and, after stirring the mixture for 30 minutes, a thick white paste forms in the bottom of the flask. The layers are separated, and the organic layer is filtered through a pad of Celite. The thick white paste is then rinsed with two 500 ml portions of methylene chloride and filtered through the Celite. The combined organic layers are then concentrated in vacuo to afford a colorless oil. The oil is then dried at room temperature under high vacuum overnight to yield the desired compound as a colorless oil (85% yield; and 96% optical purity).

(e) Preparation of the R-isomer of 2-[3-(1-Methoxy-1-methylethoxy)]propyl-2-[(octadecyloxy)methyl]oxirane In a 1-liter, 4-necked round-bottomed flask, equipped with a mechanical stirrer, internal thermometer and nitrogen inlet, is dissolved 25.5 g (0.125 mol) of the compound prepared in d) above in 250 ml of tetrahydrofuran. The resultant solution is then cooled to 0° C. and to the cooled solution is slowly added, portionwise, 10 g (0.125 mol) of sodium hydride (60% dispersion in mineral oil). The resulting suspension is then stirred for 30 minutes at 0° C. and at room temperature for 1 hour. To the suspension is successively added 54.1 g (0.163 mol) of n-octadecyl bromide and 13.1 g (0.0375 mol) of tetrabutylammonium iodide and the resultant suspension is heated to 45° C., maintained at this temperature for 4 hours and cooled to 0° C. 200 ml of water is then slowly added and the mixture is extracted with two 250 ml portions of hexane, washed with 500 ml of brine and concentrated in vacuo to afford a light yellow oil. The oil is then diluted with 100 ml of hexane, filtered through a pad of silica gel and washed with 500 ml of a mixture of hexane and ethyl acetate in a 97:3 ratio. The silica gel pad is then washed with 800 ml of a mixture of hexane and ethyl acetate in a 2:1 ratio. The filtrate is then concentrated in vacuo to yield the desired compound as a light yellow oil (50% yield; and ~90% optical purity).

(f) Preparation of the Title Compound

In a 1-liter, round-bottomed flask, equipped with a mechanical stirrer and a nitrogen inlet, are added 29.3 g (0.0625 mol) of the compound prepared in e) above, 37.5 g (0.625 mol) of acetic acid and 0.251 g (1 mmol) of the pyridinium salt of p-toluene sulfonic acid. The mixture is then stirred at room temperature for 36 hours, neutralized with 400 ml of a saturated sodium bicarbonate solution, extracted with two 200 ml portions of ethyl acetate, washed with 300 ml of brine and concentrated in vacuo to yield the desired compound as a white solid which, on recrystallization in hexane, yields the desired compound (80% yield; and 99% optical purity).

EXAMPLE 2

The following describes the preparation of the S-isomer of 2-hydroxymethyl-2-octadecyloxymethyl tetrahydrofuran.

(a) Preparation of the S-isomer of 2-[3-(1-Methoxy-1-methylethoxy)]propyl-oxiranemethanol Following essentially the procedure of Example 1(d), and using in place of the (−)-diethyl tartrate (unnatural DET), an approximately equivalent amount of (+)-diethyl tartrate (natural DET), the desired compound was obtained as a colorless oil (~85% yield; and ~90% optical purity).

(b) Preparation of the S-isomer of 2-[3-(1-Methoxy-1-methylethoxy)]propyl-2-[(octadecyloxy)methyl]oxirane Following essentially the procedure of Example 1(e), and using in place of the compound prepared in 1(d), an approximately equivalent amount of the compound prepared in a) above, the desired compound was obtained as a light yellow oil (~50% yield; and ~90% optical purity).

(c) Preparation of the Title Compound

Following essentially the procedure in the last step for preparing the compound of Example 1, and using in place of the compound prepared in 1(e), an approximately equivalent amount of the compound prepared in (b) above, the desired compound was obtained as a white solid (80% yield; and 99% optical purity).

What is claimed is:

1. A process for preparing the R-isomer of 2-hydroxymethyl-2-octadecyloxymethyl-tetrahydrofuran having the formula

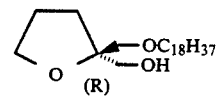

comprising the steps of:
a) reacting either 3-chloro- or 3-bromopropanol with 2-methoxypropene in the presence of the pyridinium salt of p-toluenesulfonic acid to obtain a compound having the formula

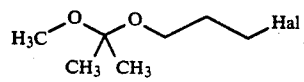

where Hal is chloro or bromo;
b) alkylating diethylmalonate with a compound prepared in step a) in the presence of an alcoholic solution of sodium ethoxide and an alkali metal iodide to obtain a malonic diester having the formula

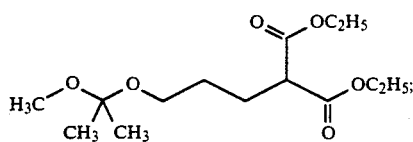

c) in a first part, reacting the diester compound prepared in step b) with an alkali metal hydride and, in a second part, reducing the compound prepared in the first part with sodium bis(2-methoxyethoxy)aluminum hydride to obtain an allylic alcohol having the formula

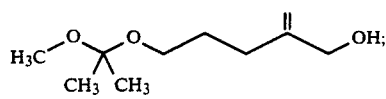

d) subjecting the allylic alcohol prepared in step c) to metal-catalyzed asymmetric Sharpless epoxidation employing a system consisting of titanium tetraisopropoxide, (−)-diethyl tartrate and t-butyhydroperoxide to obtain an epoxy alcohol having the formula

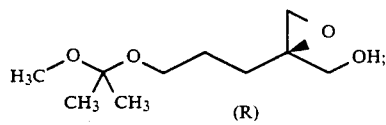

e) alkylating the epoxy alcohol prepared in step d) with n-octadecyl bromide in the presence of an alkali metal hydride and tetrabutylammonium iodide to obtain an oxirane compound having the formula

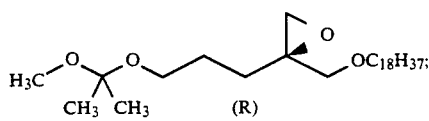

and f) reacting the oxirane compound prepared in step e) with acetic acid in the presence of the pyridinium salt of p-toluenesulfonic acid to obtain the desired R-isomer of 2-hydroxymethyl-2-octadecyloxymethyl-tetrahydrofuran.

2. A process according to claim 1 wherein 3-chloropropanol is reacted with 2-methoxypropene in step a).

3. A process according to claim 2 wherein the reaction is conducted at a temperature between −30° and 30° C.

4. A process according to claim 1 wherein diethylmalonate is alkylated with 1-chloro-3-(1-methoxy-1-methylethoxy)-propane in step b) in the presence of an ethanolic solution of sodium ethoxide and sodium iodide.

5. A process according to claim 4 wherein the alkylation is conducted at a temperature between 60° and 100° C.

6. A process according to claim 1 wherein in the first part of step c), the diester is reacted with sodium hydride in the presence of an aromatic hydrocarbon.

7. A process according to claim 6 wherein the reaction is conducted in the presence of toluene at reflux temperature.

8. A process according to claim 1 wherein the reduction in the second part of step c) is conducted in the presence of an aromatic hydrocarbon.

9. A process according to claim 8 wherein the reduction is conducted in the presence of toluene at a temperature between 70° and 100° C.

10. A process according to claim 1 wherein the epoxidation in step d) is conducted in the presence of a mixture of isooctane and an aliphatic, chlorinated hydrocarbon.

11. A process according to claim 10 wherein the epoxidation is conducted in the presence of a mixture of isooctane and methylene chloride at a temperature between −30° and −10° C.

12. A process according to claim 1 wherein the alkylation in step e) is conducted with sodium hydride and tetrabutylammonium iodide in the presence of a cyclic ether.

13. A process according to claim 12 wherein the alkylation is conducted in the presence of tetrahydrofuran at between 0° C. and the reflux temperature.

14. A process according to claim 1 wherein step f) is conducted at a temperature between 15° and 40° C.

15. A process according to claim 1 comprising the steps of:

a) reacting 3-chloropropanol with 2-methoxypropene in the presence of the pyridinium salt of p-toluenesulfonic acid at a temperature between −30° and 30° C. to obtain the compound having the formula

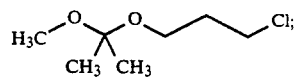

b) alkylating diethylmalonate with the compound prepared in step a) in the presence of an ethanolic solution of sodium ethoxide and sodium iodide at a temperature between 60° C. and 100° C. to obtain a malonic diester having the formula

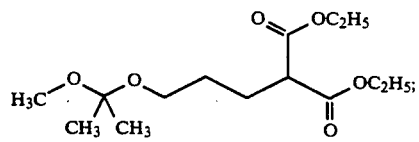

c) in a first part, reacting the diester compound prepared in step b) with sodium hydride in the presence of toluene at reflux temperature and, in a second part, reducing the compound prepared in the first part with sodium bis(2-methoxyethoxy) aluminum hydride in the presence of toluene at a temperature between 70° and 100° C. to obtain an allylic alcohol having the formula

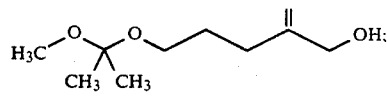

d) subjecting the allylic alcohol prepared in step c) to metal-catalyzed asymmetric Sharpless epoxidation employing a system consisting of titanium tetraisopropoxide, (−)-diethyl tartrate and t-butyl hydroperoxide in the presence of a mixture of isooctane and methylene chloride at a temperature between −30° and −10° C. to obtain an epoxy alcohol having the formula

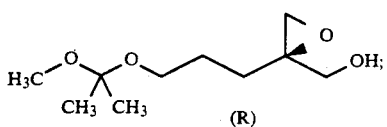

e) alkylating the epoxy alcohol prepared in step d) with n-octadecyl bromide in the presence of sodium hydride, tetrabutylammonium iodide and tetrahydrofuran at between 0° C. and the reflux temperature of the solvent to obtain an oxirane compound having the formula

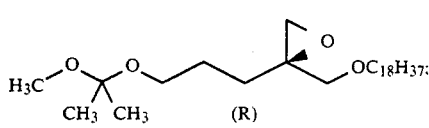

and f) reacting the oxirane compound prepared in step e) with acetic acid in the presence of the pyridinium salt of p-toluenesulfonic acid at a temperature between 15° and 40° C. to obtain the R-isomer of 2-hydroxymethyl-2-octadecyloxymethyl-tetrahydrofuran.

16. A process for preparing the S-isomer of 2-hydroxymethyl-2-octadecyloxymethyl-tetrahydrofuran having the formula

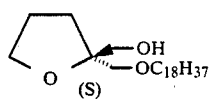

comprising the steps of:

a) reacting either 3-chloro- or 3-bromopropanol with 2-methoxypropene in the presence of the pyridinium salt of p-toluenesulfonic acid to obtain a compound having the formula

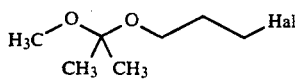

where Hal is chloro or bromo;

b) alkylating diethylmalonate with a compound prepared in step a) in the presence of an alcoholic solution of sodium ethoxide and an alkali metal iodide to obtain a malonic diester having the formula

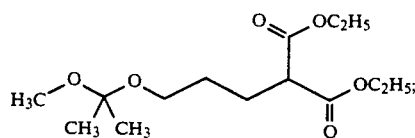

c) in a first part, reacting the diester compound prepared in step b) with an alkali metal hydride and, in a second part, reducing the compound prepared in the first part with sodium bis(2-methoxyethoxy) aluminum hydride to obtain an allylic alcohol having the formula

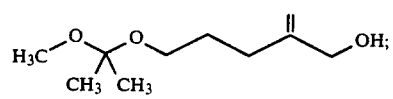

d) subjecting the allylic alcohol prepared in step c) to metal-catalyzed asymmetric Sharpless epoxidation employing a system consisting of titanium tetraisopropoxide, (+)-diethyl tartrate and t-butylhydroperoxide to obtain an epoxy alcohol having the formula

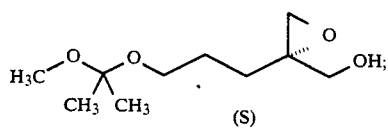

e) alkylating the epoxy alcohol prepared in step d) with n-octadecyl bromide in the presence of an alkali metal hydride and tetrabutylammonium iodide to obtain an oxirane compound having the formula

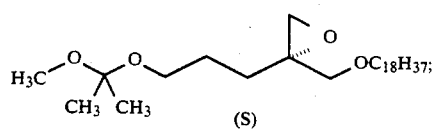

and f) reacting the oxirane compound prepared in step e) with acetic acid in the presence of the pyridinium salt of p-toluenesulfonic acid to obtain the desired S-isomer of 2-hydroxymethyl-2-octadecyloxymethyltetrahydrofuran.

17. A process according to claim 16 wherein 3-chloropropanol is reacted with 2-methoxypropene in step a).

18. A process according to claim 17 wherein the reaction is conducted at a temperature between −30° and 30° C.

19. A process according to claim 16 wherein diethylmalonate is alkylated with 1-chloro-3-(1-methoxy-1-methylethoxy)-propane in step b) in the presence of an ethanolic solution of sodium ethoxide and sodium iodide.

20. A process according to claim 19 wherein the alkylation is conducted at a temperature between 60° and 100° C.

21. A process according to claim 16 wherein in the first part of step c), the diester is reacted with sodium hydride in the presence of an aromatic hydrocarbon.

22. A process according to claim 21 wherein the reaction is conducted in the presence of toluene at reflux temperature.

23. A process according to claim 16 wherein the reduction in the second part of step c) is conducted in the presence of an aromatic hydrocarbon.

24. A process according to claim 23 wherein the reduction is conducted in the presence of toluene at a temperature between 70° and 100° C.

25. A process according to claim 16 wherein the epoxidation in step d) is conducted in the presence of a mixture of isooctane and an aliphatic, chlorinated hydrocarbon.

26. A process according to claim 25 wherein the epoxidation is conducted in the presence of a mixture of isooctane and methylene chloride at a temperature between −30° and −10° C.

27. A process according to claim 16 wherein the alkylation in step e) is conducted with sodium hydride and tetrabutylammonium iodide in the presence of a cyclic ether.

28. A process according to claim 27 wherein the alkylation is conducted in the presence of tetrahydrofuran at between 0° C. and the reflux temperature of the solvent.

29. A process according to claim 16 wherein step f) is conducted at a tempreature between 15° and 40° C.

30. A process according to claim 16 comprising the steps of:

a) reacting 3-chloropropanol with 2-methoxypropene in the presence of the pyridinium salt of p-toluenesulfonic acid at a temperature between −30° and 30° C. to obtain the compound having the formula

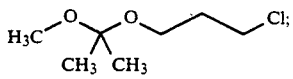

b) alkylating diethylmalonate with the compound prepared in step a) in the presence of an ethanolic solution of sodium ethoxide and sodium iodide at a temperature between 60° and 100° C. to obtain a malonic diester having the formula

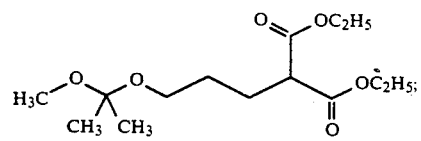

c) in a first part, reacting the diester compound prepared in step b) with sodium hydride in the presence of toluene at reflux temperature and, in a second part, reducing the compound prepared in the first part with sodium bis(2-methoxyethoxy) aluminum hydride in the presence of toluene at a temperature between 70° and 100° C. to obtain an allylic alcohol having the formula

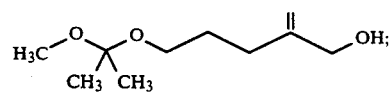

d) subjecting the allylic alcohol prepared in step c) to metal-catalyzed asymmetric Sharpless expoxidation employing a system consisting of titanium tetraisopropoxide, (+)-diethyltartrate and t-butyl hydroperoxide in the presence of a mixture of isooctane and methylene chloride at a temperature between −30° and −10° C. to obtain an epoxy alcohol having the formula

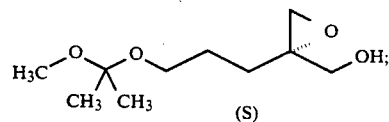

e) alkylating the epoxy alcohol prepared in step d) with n-octadecyl bromide in the presence of sodium hydride, tetrabutylammonium iodide and tetrahydrofuran at between 0° C. and the reflux temperature of the solvent to obtain an oxirane compound having the formula

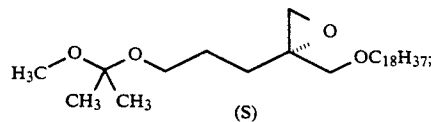

and f) reacting the oxirane compound prepared in step e) with acetic acid in the presence of the pyridinium salt of p-toluenesulfonic acid at a temperature between 15° and 40° C. to obtain the S-isomer of 2-hydroxymethyl-2-octadecyloxymethyl-tetrahydrofuran.

* * * * *